US009056015B2

(12) United States Patent
Zehavi et al.

(10) Patent No.: US 9,056,015 B2
(45) Date of Patent: Jun. 16, 2015

(54) SEGMENTED INSERT FOR INTERVERTEBRAL SUPPORT

(71) Applicant: MAZOR ROBOTICS LTD., Caesaria, IL (US)

(72) Inventors: Eli Zehavi, Haifa (IL); Moshe Shoham, Hoshaya (IL)

(73) Assignee: MAZOR ROBOTICS LTD., Caesaria (IL)

(*) Notice: Subject to any disclaimer, the term of this patent is extended or adjusted under 35 U.S.C. 154(b) by 179 days.

(21) Appl. No.: 13/709,448

(22) Filed: Dec. 10, 2012

(65) Prior Publication Data

US 2013/0096682 A1    Apr. 18, 2013

Related U.S. Application Data

(63) Continuation of application No. 12/922,457, filed as application No. PCT/IL2009/000292 on Mar. 15, 2009, now Pat. No. 8,328,852.

(60) Provisional application No. 61/064,610, filed on Mar. 14, 2008.

(51) Int. Cl.
*A61B 17/70* (2006.01)
*A61F 2/44* (2006.01)
*A61F 2/30* (2006.01)

(52) U.S. Cl.
CPC ............... *A61F 2/44* (2013.01); *A61F 2/4455* (2013.01); *A61F 2002/30172* (2013.01); *A61F 2002/30446* (2013.01); *A61F 2002/30471* (2013.01);
(Continued)

(58) Field of Classification Search
CPC .............................. A61F 2/442; A61F 2/4611

USPC ................................ 606/249; 623/17.11–17.16
See application file for complete search history.

(56) References Cited

U.S. PATENT DOCUMENTS 3,397,699 A * 8/1968 Kohl .............................. 604/105
4,913,164 A * 4/1990 Greene et al. ................. 607/126
(Continued)

FOREIGN PATENT DOCUMENTS

DE    20314708 U1    11/2003
EP    1552797 A2    7/2005

OTHER PUBLICATIONS

Extended European search report of the European Patent Office in corresponding European patent application No. 09721191.6, dated Mar. 7, 2013.

*Primary Examiner* — Eduardo C Robert
*Assistant Examiner* — Stuart S Bray
(74) *Attorney, Agent, or Firm* — Daniel Feigelson; Fourth Dimension IP

(57) ABSTRACT

A spinal intervertebral support implant, for fusion or for dynamic stabilization purposes. A rod, preferably in the form of a screw, is inserted obliquely from the pedicle of an inferior vertebra into the body of a neighboring superior vertebra, through the disc space. The rod can be anchored into the body of the superior vertebra by means of a force fit or a screw thread. A pile of elements is disposed on the rod in the disc space like a pile of washers, so that the compression load between vertebrae is carried partly by these elements. These elements can be inserted through the bore through which the rod was inserted in a tightly folded configuration, and deployed into their washer-like form only when in position in the intervertebral space, such that there is no need for any additional incisions.

20 Claims, 9 Drawing Sheets

(52) U.S. Cl.
CPC ............... *A61F2002/30563* (2013.01); *A61F 2002/30579* (2013.01); *A61F 2002/30596* (2013.01); *A61F 2002/30599* (2013.01); *A61F 2002/30604* (2013.01); *A61F 2002/3085* (2013.01); *A61F 2002/4415* (2013.01); *A61F 2220/0041* (2013.01); *A61F 2220/0091* (2013.01); *A61F 2230/0052* (2013.01); *A61F 2250/0063* (2013.01)

(56) References Cited

U.S. PATENT DOCUMENTS

| | | | |
|---|---|---|---|
| 6,595,998 B2 * | 7/2003 | Johnson et al. | 606/90 |
| 6,692,495 B1 * | 2/2004 | Zacouto | 606/247 |
| 7,153,305 B2 * | 12/2006 | Johnson et al. | 606/90 |
| 7,166,131 B2 * | 1/2007 | Studer et al. | 623/17.16 |
| 7,311,713 B2 * | 12/2007 | Johnson et al. | 606/90 |
| 7,666,226 B2 * | 2/2010 | Schaller | 623/17.11 |
| 7,731,751 B2 * | 6/2010 | Butler et al. | 623/17.11 |
| 7,744,637 B2 * | 6/2010 | Johnson et al. | 606/279 |
| 7,780,707 B2 * | 8/2010 | Johnson et al. | 606/279 |
| 7,780,734 B2 * | 8/2010 | Johnson et al. | 623/17.16 |
| 7,811,331 B2 * | 10/2010 | Johnson et al. | 623/17.16 |
| 7,905,885 B2 * | 3/2011 | Johnson et al. | 606/90 |
| 7,905,905 B2 * | 3/2011 | Cragg et al. | 606/246 |
| 7,967,867 B2 * | 6/2011 | Barreiro et al. | 623/17.16 |
| 8,075,623 B2 * | 12/2011 | Johnson et al. | 623/17.16 |
| 8,123,755 B2 * | 2/2012 | Johnson et al. | 606/90 |
| 8,328,852 B2 * | 12/2012 | Zehavi et al. | 606/279 |
| 8,343,193 B2 * | 1/2013 | Johnson et al. | 606/279 |
| 8,454,617 B2 * | 6/2013 | Schaller et al. | 606/90 |
| 8,790,375 B2 * | 7/2014 | Ali | 606/279 |
| 2002/0183761 A1 * | 12/2002 | Johnson et al. | 606/90 |
| 2004/0019354 A1 * | 1/2004 | Johnson et al. | 606/90 |
| 2004/0220580 A1 * | 11/2004 | Johnson et al. | 606/90 |
| 2005/0055097 A1 * | 3/2005 | Grunberg et al. | 623/17.11 |
| 2005/0107878 A1 * | 5/2005 | Conchy | 623/17.11 |
| 2005/0143827 A1 * | 6/2005 | Globerman et al. | 623/17.16 |
| 2005/0171552 A1 * | 8/2005 | Johnson et al. | 606/90 |
| 2005/0187558 A1 * | 8/2005 | Johnson et al. | 606/90 |
| 2005/0261684 A1 * | 11/2005 | Shaolian et al. | 606/61 |
| 2005/0273166 A1 * | 12/2005 | Sweeney | 623/17.11 |
| 2006/0161166 A1 * | 7/2006 | Johnson et al. | 606/90 |
| 2006/0189999 A1 * | 8/2006 | Zwirkoski | 606/90 |
| 2006/0224241 A1 * | 10/2006 | Butler et al. | 623/17.15 |
| 2007/0055271 A1 * | 3/2007 | Schaller | 606/90 |
| 2007/0055272 A1 * | 3/2007 | Schaller | 606/90 |
| 2007/0173939 A1 * | 7/2007 | Kim et al. | 623/17.11 |
| 2007/0179612 A1 * | 8/2007 | Johnson et al. | 623/17.11 |
| 2007/0233260 A1 * | 10/2007 | Cragg | 623/17.12 |
| 2008/0027437 A1 * | 1/2008 | Johnson et al. | 606/61 |
| 2008/0027453 A1 * | 1/2008 | Johnson et al. | 606/90 |
| 2008/0027454 A1 * | 1/2008 | Johnson et al. | 606/90 |
| 2008/0039842 A1 * | 2/2008 | Sweeney | 606/61 |
| 2009/0112318 A1 * | 4/2009 | Butler et al. | 623/16.11 |
| 2009/0171393 A9 * | 7/2009 | Johnson et al. | 606/247 |
| 2009/0177207 A1 * | 7/2009 | Schaller | 606/93 |
| 2009/0182386 A1 * | 7/2009 | Schaller | 606/86 R |
| 2009/0234361 A9 * | 9/2009 | Johnson et al. | 606/90 |
| 2010/0174288 A1 * | 7/2010 | Schaller | 606/90 |
| 2010/0174289 A1 * | 7/2010 | Schaller | 606/99 |
| 2010/0174375 A1 * | 7/2010 | Schaller | 623/17.16 |
| 2011/0009870 A1 * | 1/2011 | Johnson et al. | 606/90 |
| 2011/0009971 A1 * | 1/2011 | Johnson et al. | 623/17.16 |
| 2011/0040386 A1 * | 2/2011 | Kim et al. | 623/17.16 |
| 2011/0264228 A1 * | 10/2011 | Johnson et al. | 623/17.16 |
| 2012/0158003 A1 * | 6/2012 | Johnson et al. | 606/92 |
| 2012/0158141 A1 * | 6/2012 | Johnson et al. | 623/17.11 |
| 2012/0197299 A1 * | 8/2012 | Fabian, Jr. | 606/279 |
| 2012/0197405 A1 * | 8/2012 | Cuevas et al. | 623/17.16 |
| 2013/0096682 A1 * | 4/2013 | Zehavi et al. | 623/17.11 |
| 2013/0310943 A1 * | 11/2013 | McCormack et al. | 623/17.16 |
| 2014/0046333 A1 * | 2/2014 | Johnson et al. | 606/90 |

\* cited by examiner

SEGMENTED INSERT FOR INTERVERTEBRAL SUPPORT

RELATED APPLICATIONS

This application is a continuation of U.S. Ser. No. 12/922,457, which is a §371 application of PCT/IL2009/000292, filed Mar. 15, 2009. This application and claims the benefit under 35 U.S.C. §120 of the '457 application as well as said PCT application, and further claims the benefit under 35 U.S.C. §119(e) of U.S. Provisional Patent Application U.S. Ser. No. 61/064,610, filed Mar. 14, 2008. The contents of these priority applications are incorporated herein by reference.

FIELD OF THE INVENTION

The present invention relates to the field of support inserts for stabilizing or fusing adjacent vertebrae, especially using elements inserted under minimally invasive procedures.

BACKGROUND OF THE INVENTION

Stabilization of the spine generally utilizes implants such as screws, cages, hooks, spacers, and other devices, to stabilize two or more adjacent vertebrae. Traditionally, two adjacent vertebrae are fixed to each other in a stable, mutual position, and fusion is induced by means of bone growth. Recently, dynamic stabilization of the spine has also been introduced, in which two vertebrae are stabilized but not fused, so that the relative motion between the vertebrae is preserved. In both cases, however, implants are used to maintain the relative posture of the two vertebrae.

A common procedure for spine stabilization uses pedicle screws on either side of the spine and a cage, where the pedicle screws and a connected rod support the spine posteriorly, while a cage inserted into the disc space provides support at the anterior side of the adjacent vertebrae. The cage may be inserted in a number of different ways, the most common currently in use including:
(i) anteriorly, in a procedure known as Anterior Lumber Interbody Fusion (ALIF),
(ii) posteriorly in a procedure known as Posterior Lumber Interbody Fusion (PLIF), or
(iii) lateraly in a procedure known as Transforaminal Lumber Interbody Fusion (TLIF).

Other options also exist, but with the exception of the procedure known as Axial Lumbar Interbody Fusion (AxiaLIF®) developed by Trans1 Inc of Wilmington, N.C., USA, all the other approaches reach the disc space within the transverse plane. The AxiaLIF® procedure has been described as useable between only one or two lumbar levels, with only the L5-S1 fusion procedure being publically advertised.

In U.S. Pat. No. 7,241,297 to S. M. Shaolian et al., there are described methods of inserting elements intervertabrally through a curved passage drilled from the pedicle to the intervertebral space. In order to negotiate such a narrow curved passage, tightly coiled elements of shape memory material are used. No additional screw support between the vertebrae is provided, such that only compression forces are handled by this method.

Reference is now made to FIG. 1, which is a cut-away drawing illustrating schematically a suggested procedure known as Trans-Pedicular Lumbar Interbody Fusion (TPLIF) also termed Guided Oblique Lumbar Interbody Fusion (GOLIF), in which the approach is oblique, from the pedicle 10 of an inferior vertebra 12 through the disc space 13 and into the adjacent superior vertebra body 14. The use of this angular oblique entry enables the screw to connect both vertebrae with a straight screw 16, which has a thread which is driven into the superior vertebra body 14, and is affixed at its other end preferably by means of a threaded fixture into the pedicle 10 of the inferior vertebra. One such screw is inserted on either side of the spine. Specific implementations of the GOLIF method are described in co-pending Provisional Patent Applications, No. 61/193,441 for "Guided Oblique Spinal Inter-body Fusion" and No. 61/193,586 for "Double Threaded Orthopedic Screw", both having co-inventors with the present application.

Additional support for this fixation method, when needed, may be obtained using an intervertebral body such as a cage. However, insertion of such cage support devices is generally performed by fairly invasive methods, and it would be advantageous to devise a less invasive method of performing the complete GOLIF procedure.

The disclosures of each of the publications mentioned in this section and in other sections of the specification, are hereby incorporated by reference, each in its entirety.

SUMMARY OF THE INVENTION

The present claimed invention relates to a novel type of implant used to maintain the relative posture of two adjacent vertebrae, either for fusion or for dynamic stabilization purposes. The difference between these procedures is that whereas fusion requires insertion of bone-grafting material to encourage intervertebral bone growth, in the case of dynamic stabilization, no disc morselization is generally performed, or only sufficient to leave space for the intervertebral body, nor is any intervertebral bone-growth promotion used.

In the procedures described in this disclosure, a rod, preferably in the form of a screw, is inserted obliquely from the pedicle of an inferior vertebra into the body of the neighboring superior vertebra, through the disc space. The rod can be anchored into the body of the superior vertebra by means of a forced fit, or by having openings in its end portion and using bone cement or bone growth promoting material to create a firm bond to the vertebral bone, or the rod can be threaded like a screw. Since such a threaded rod implementation may be considered as providing a simpler fixation method, the plain rod being required usually only when the vertebral cancellous bone structure is not sufficiently strong to support a screw thread, such as in osteoporotic bone, the screw implementation will be used as the descriptive example throughout the rest of this application, though it is to be understood that this implementation is not intended to limit the scope of this application. For dynamic stabilization use, it may be more advantageous if the rod is not fixed in both of the superior and inferior vertebral body, and possible implementations where it is not rigidly fixed in either are also possible, as will be described hereinbelow.

Once the screw is in place, further support is provided in the form of a pile of elements, strung on the screw like a pile of washers, and added inside the intervertebral disc space, so that the compression load between vertebrae is carried partly by these washer-like elements. This increases spine stability, reduces the loads on the screw in those cases where the screw too is used for support, and can assist in achieving decompression. These inter-vertebral washer-like elements are inserted through the bore in which the screw was is inserted, onto the screw shank in a tightly folded configuration, and are deployed into their flat washer-like form only when in position in the intervertebral space. The washer-like elements are therefore inserted through the same hole as the screw, without the need for any additional incisions. The bore is typically of the order of 6 mm in diameter, such that the procedure is minimally invasive. Since the bore is drilled from the pedicle of one vertebra and directed obliquely to the disc space, the washer-like element insertion is not performed in the transverse plane, as is a common practice for prior art cage insertion.

Each washer-like element can be regarded as a folded support before insertion. After insertion, the intervertebral support, added to the already present screw support, thus consists of a pile of several metal or plastic washers, which are collectively termed in this disclosure, a segmented support insert. Since, at least for a fusion procedure, the disc's nucleus polposus is first cleaned out surgically, a space is generated into which the washer-like elements are expanded.

For fusion use, the washer-like elements can be essentially flat, while for dynamic stabilization use, the elements can be in the form of spring or dished washers, with the leaves of the element having a curved shape, as will be further explained hereinbelow. In the latter case, they should most advantageously be strung on the support screw in pairs with their convex sides in contact, so as to provide some element of springiness between the vertebrae during mutual linear motion of the vertebrae. The curvature also assists in execution of any mutual angular motion which may take place.

There is thus provided in this disclosure, a first example implementation of a system for providing support between two adjacent vertebrae of a subject, the system comprising:
(i) a rod for affixing in the body of a first one of the vertebrae, and adapted to be inserted through a bore in the pedicle of the second one of the vertebrae, and
(ii) at least one element adapted to be strung onto the rod and into the intervertebral region, the at least one element being of initial dimensions such that it passes through the bore, and is adapted to deploy in the intervertebral region to a form having lateral dimensions substantially larger than that of the bore.

In such a system, the at least one element may be a plurality of elements, such that when deployed in the intervertebral region, the plurality of elements essentially fills the height of the intervertebral region. This plurality of elements and the rod may then provide support between the adjacent vertebrae. Furthermore, the at least one deployed element may have an essentially flattened form or a dished form.

Additional implementations may involve a system in which the rod is a screw having at least one threaded portion. In such cases, the at least one threaded portion may be adapted to be screwed into the body of the first one of the vertebrae, or affixed into the pedicle of the second one of the vertebrae. Additionally, the system may include a cap adapted to be fixed to the pedicle to prevent the rod from retracting from the vertebrae.

In any of the previously described examples of this system, at least one of the elements may comprise a cylinder whose wall has a number of longitudinal slots along a part of its length, the slots being positioned at spaced angular locations around the circumference of the cylinder. In such a case, the slotted sections of the wall of the cylinder may be such that they bend radially outwards within the intervertabral region, so as to form an element form having lateral dimensions substantially larger than that of the bore. This outward bending can be facilitated by means of openings formed in the slots, such that the slotted sections of the wall bend preferentially between the openings. Alternatively, the element may further comprise at least one circumferential groove formed on the cylinder wall, such that the slotted sections of the wall bend preferentially at the at least one circumferential groove, or at least one mechanical joint formed in the cylinder wall, such that a slotted section of the wall bends preferentially at the at least one mechanical joint.

In any of those implementations involving slotted walls, that end of the cylinder from which the longitudinal slots commence may advantageously be chamfered in a direction which assists in the radially outward bending of the slotted sections of the wall. Furthermore, the rod may have a sloped shoulder to contact the chamfered end of the cylinder, to assist in the radially outward bending of the slotted sections of the wall.

In any of the previously described exemplary systems, at least one of the elements may comprise a shape memory alloy.

Yet other implementations perform a method of providing support between two adjacent vertebrae of a subject, the method comprising:
(i) providing a rod for affixing in the body of a first one of the vertebrae,
(ii) drilling a bore in the pedicle of the second one of the vertebrae,
(iii) inserting the rod through the bore and fixing it into the body of the first one of the vertebrae,
(iv) providing at least one element having initial dimensions such that it passes through the bore, and being adapted to deploy to a form having lateral dimensions substantially larger than that of the bore when disposed in the intervertebral region, and
(v) stringing the at least one element onto the rod and into the intervertebral region, such that the at least one element can deploy therein.

In such a method, the at least one element may be a plurality of elements, the method further comprising the step of sliding the plurality of elements into the intervertebral region until the plurality of elements essentially fill the height of the intervertebral region.

This plurality of elements and the rod may then be used to provide support between the adjacent vertebrae. Furthermore, the at least one deployed element may have an essentially flattened form or a dished form.

Additional implementations may involve a method in which the rod is a screw having at least one threaded portion. Such methods may include the additional step of screwing the at least one threaded portion into the body of the first one of the vertebrae, or affixing the at least one threaded portion into the pedicle of the second one of the vertebrae. Additionally, the method may include the step of fixing a cap to the pedicle to prevent the rod from retracting from the vertebrae.

In any of the previously described examples of such methods, at least one of the elements may comprise a cylinder whose wall has a number of longitudinal slots along a part of its length, the slots being positioned at spaced angular locations around the circumference of the cylinder. In such a case, the slotted sections of the wall of the cylinder may be such that they bend radially outwards within the intervertabral region, so as to form an element form having lateral dimensions substantially larger than that of the bore. This outward bending can be facilitated by providing the slots with openings, such that the slotted sections of the wall bend preferentially between the openings. Alternatively, the element may be constructed to have at least one circumferential groove formed on the cylinder wall, such that the slotted sections of the wall bend preferentially at the at least one circumferential groove, or to have at least one mechanical joint formed in the cylinder wall, such that a slotted section of the wall bends preferentially at the at least one mechanical joint.

In any of those implementations of methods involving the use of cylindrical elements with slotted walls, that end of the cylinder from which the longitudinal slots commence may advantageously be chamfered in a direction which assists in the radially outward bending of the slotted sections of the wall. Furthermore, the rod may have a sloped shoulder to contact the chamfered end of the cylinder, to assist in the radially outward bending of the slotted sections of the wall.

For use in any of the previously described exemplary methods, at least one of the elements may comprise a shape memory alloy.

Finally, the term washer, rather than disc, is used generally throughout this disclosure to describe the segmental elements of the segmented support insert, and may also be thuswise claimed, in order to reserve use of the term disc for the intervertebral space, to avoid any confusion arising therefrom.

BRIEF DESCRIPTION OF THE DRAWINGS

The present invention will be understood and appreciated more fully from the detailed description, taken in conjunction with the drawings in which.

DETAILED DESCRIPTION

Figure 1:
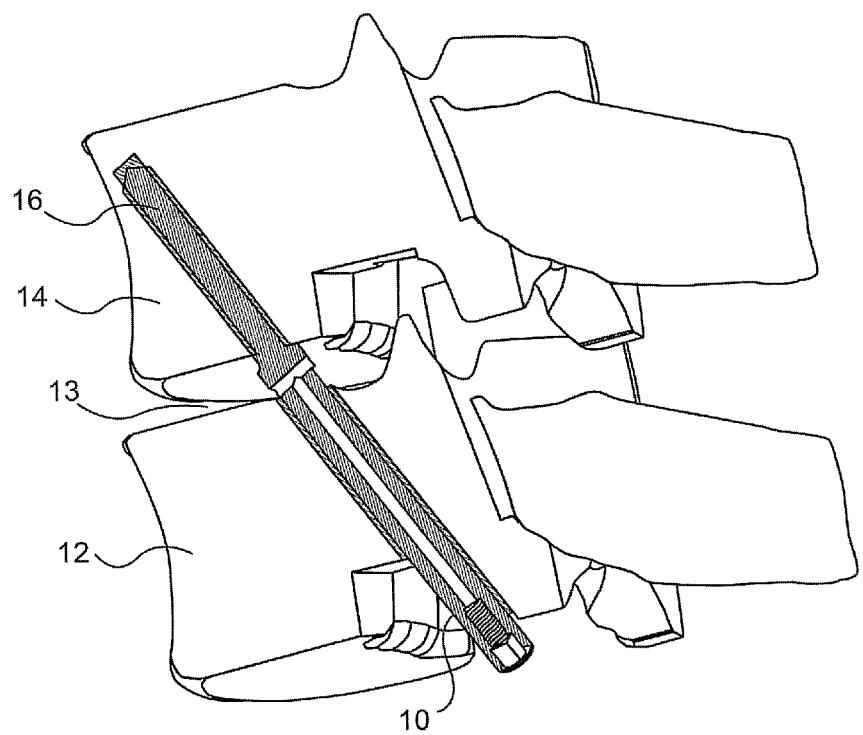
FIG. 1 is a cut-away drawing illustrating schematically the prior art Guided Oblique Lumbar Interbody Fusion (GOLIF) procedure for vertebral fusion.
Figure 2A:
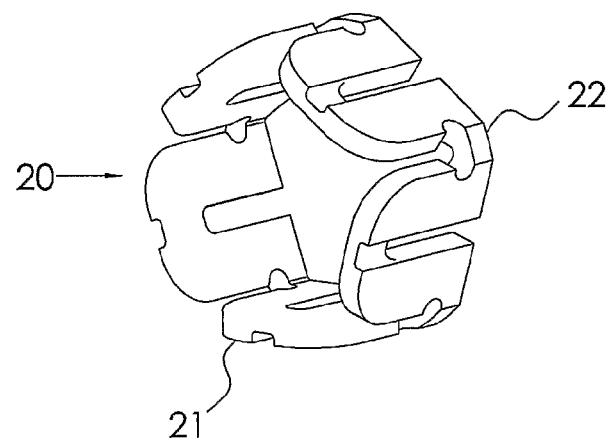
FIGS. 2A and 2B illustrate schematically the two stages of a single exemplary segmental element, before and after deployment.
Figure 2B:
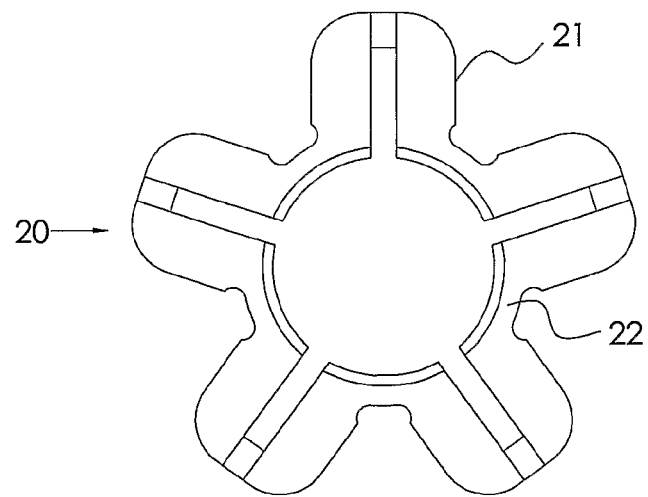

Reference is now made to FIGS. 2A and 2B, which illustrate schematically the two stages of an exemplary cylindrical segmental element 20, before and after deployment. FIG. 2A shows the element 20 with its leaves 21 folded, such that it can be inserted over the shank of the screw and through a hole drilled in the cortical bone of the pedicle of a vertebra. Once the leaves 21 protrude from the vertebra body into the disc space, they can expand into the disc space, making the segmental element almost flat and washer-like, and with a substantially larger diameter than that of the screw hole through which they were inserted. The element may be made of either a flexible or a rigid material. The leaves are connected by joints 22, which enable the leaves to rotate relative to each other around an axis parallel to their circumferential point of joining. The joints 22 can be either thinner or more flexible sections of the elements, or actual mechanical joints such as miniature revolute joints.

The radial expansion of the leaves 21 on reaching the disc space can be generated either because they are made of a springy material and are preloaded before insertion, or because the deployable leaves have a chamfered edge which is sloped in such a direction that as it is inserted over the screw, a shoulder on the screw pushes the chamfered edge of the insert, exerting a lateral force on the leaves causing them to expand radially outwards. This is shown in FIGS. 5, 6A-C and 7A-C hereinbelow. The elements can alternatively be constructed of a shape memory alloy (SMA), such as nitinol. Use can be made either of an SMA having a transition temperature above that of body temperature, such that the superelasticity properties of the material may be used to cause its deployment. Alternatively, the element can be formed in a washer shape, using a material with a transition temperature below that of body temperature, inserted in a folded state while cooled below the transition point, and allowed to warm up through its transition point once inserted into the subject's body, at which stage it regains its memory shape as a flat washer-like element.

Figure 3:
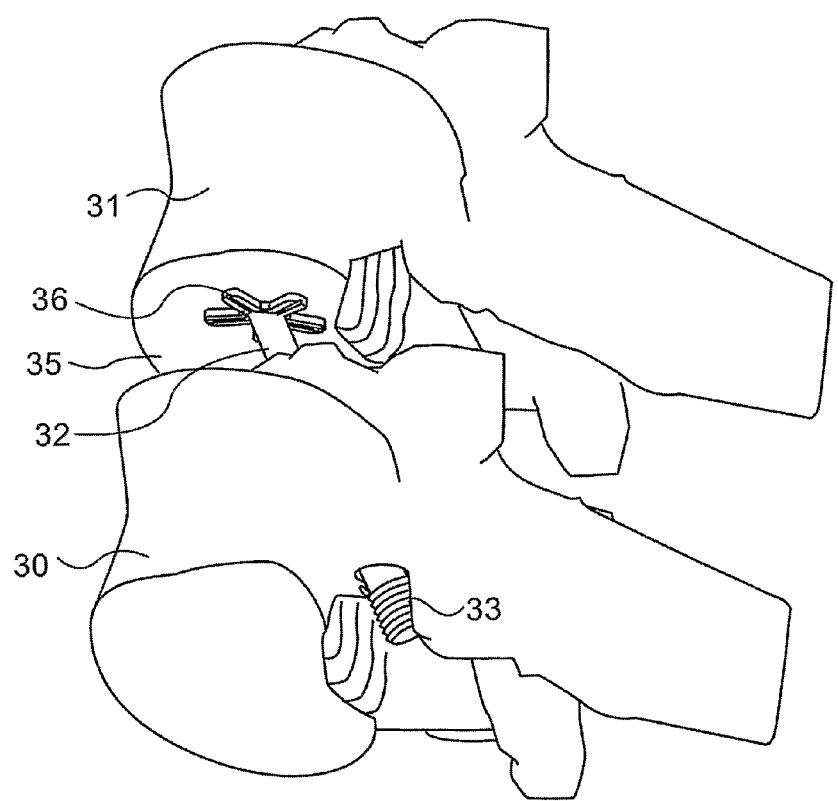
FIG. 3 illustrates schematically an isometric and partly cut-away view of a pair of adjacent vertebrae with an obliquely inserted support screw joining the vertebrae, and a single washer-like element expanded into the disc space.

Reference is now made to FIG. 3, which illustrates schematically an isometric and partly cut-away view of a pair of adjacent vertebrae 30, 31, with an obliquely inserted support screw 32 joining the vertebrae, from the pedicle 33 of the inferior vertebra 30, to the body of the superior vertebra 31, and across the disc space 35. A single washer-like element 36 is shown after insertion over the screw, and expansion into the disc space. A number of such elements are inserted until the disc space is full. It is to be understood that a second obliquely disposed screw is generally inserted on the opposite side of the spinal column. In rare cases, a single screw may be sufficient.

Figure 4A:
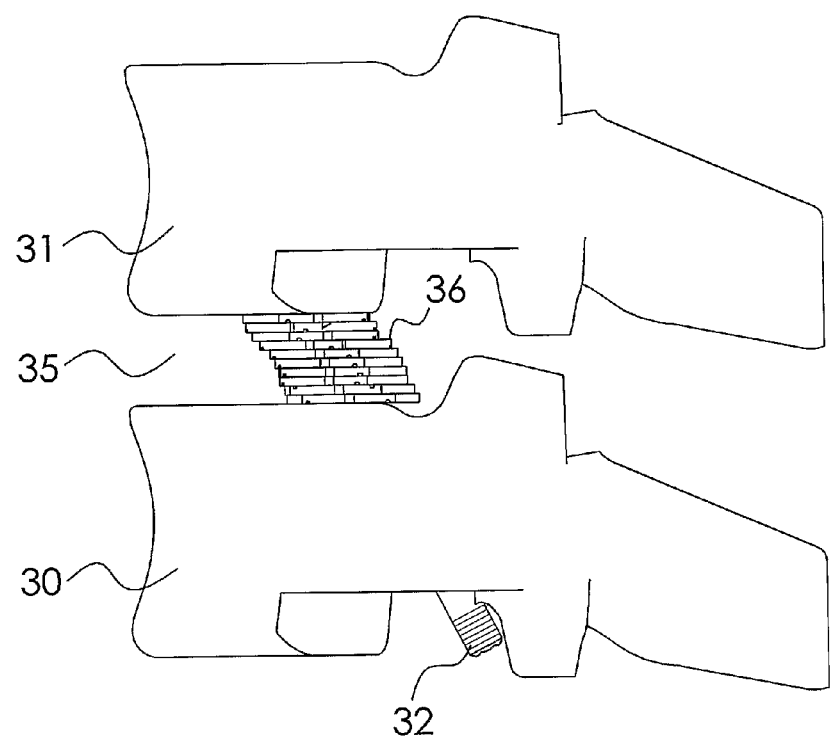
FIG. 4A illustrates schematically a lateral view of the same vertebrae in FIG. 3, but with the disc space filled with a stack of inserted expanded washer-like elements.

Reference is now made to FIG. 4A, which illustrates schematically a lateral view of the same vertebrae 30, 31 as those of FIG. 3, but now with the disc space 35 filled with a stack of inserted expanded washer-like elements 36 after insertion over the screw 32 and expansion into the disc space. As a result, the compression force between the two adjacent vertebrae is carried mainly by the segmented support insert and not by the screw itself.

Figure 4B:
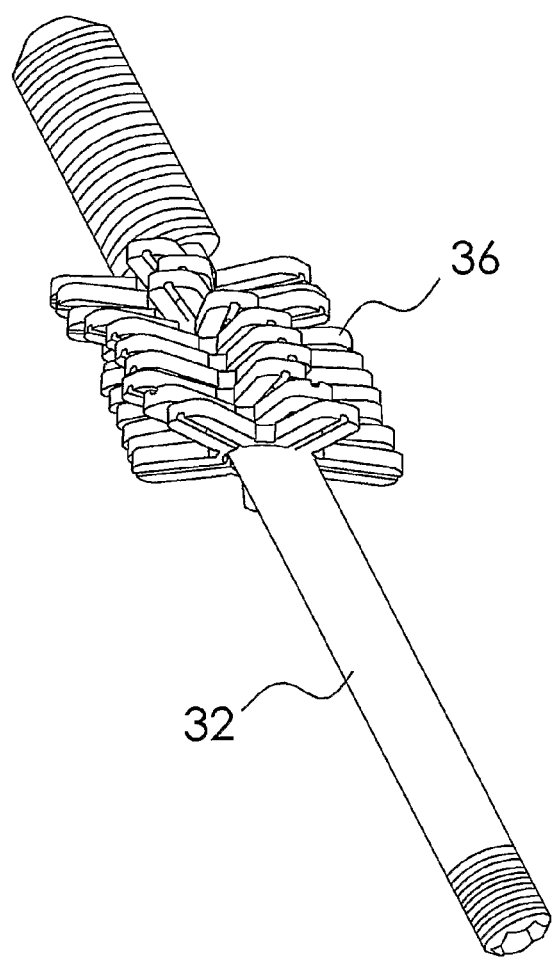
FIG. 4B illustrates schematically an isometric view of the screw of FIG. 4A, showing the washer-like elements stacked on the screw.

Reference is now made to FIG. 4B, which illustrates schematically an isometric view of the screw 32 of FIG. 4A, showing the washer-like elements 36 stacked on the screw, to form the complete segmented support insert.

Figure 5:
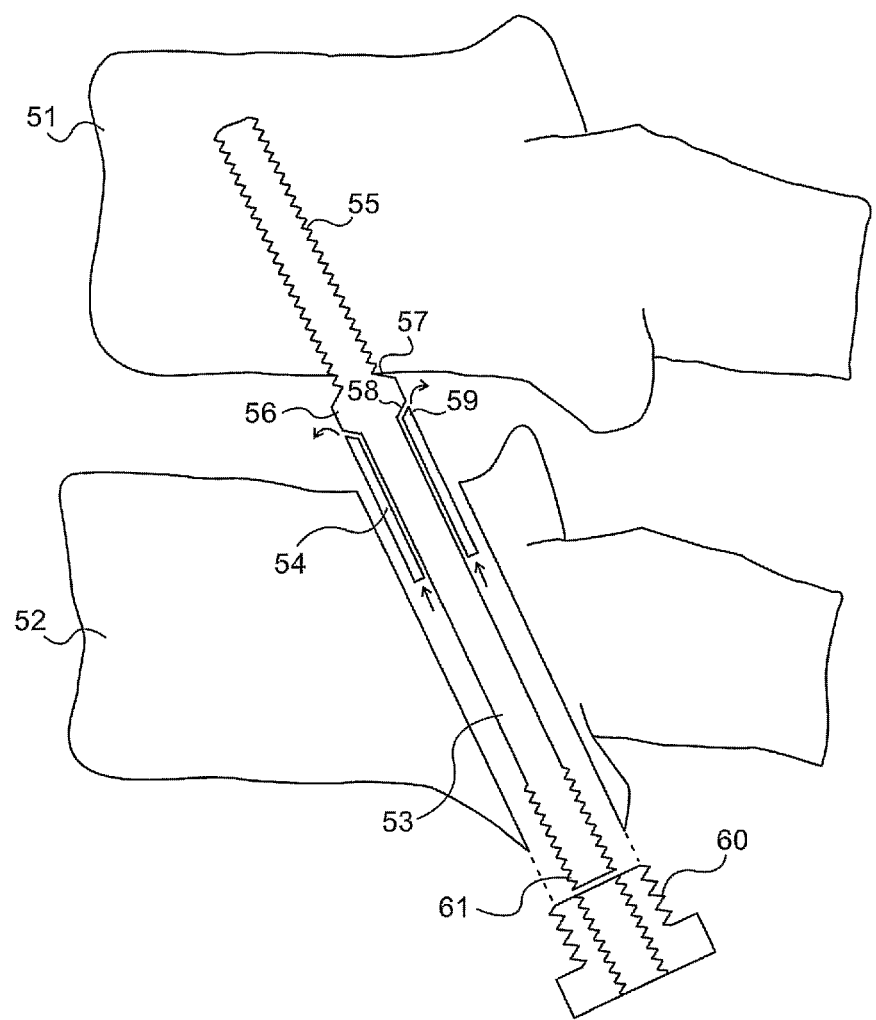
FIG. 5 is a schematic cross sectional illustration of a pair of adjacent vertebrae, with a support screw inserted.

Reference is now made to FIG. 5, which is a schematic cross sectional illustration of a pair of adjacent vertebrae, a superior vertebra 51, and an inferior vertebra 52 at which the pedicular entry is made. A hole is drilled into both vertebrae from a pedicle of the inferior vertebra, obliquely into the body of the neighbouring superior vertebra. An example screw 53 and segmental element 54 are shown. The screw has a threaded distal end section 55, which is screwed into the superior vertebral body, and a larger diameter mid section 56. This mid section may have a shoulder 57 at the distal end to limit the screw's entry into the vertebra body, and a chamfered shoulder 58 at the proximal end. The segmental element 54 is pushed, as indicated by the arrows in the drawing, against this chamfered shoulder 58 as it is forced over the screw into the intervertebral region, such that the force exerted on the chamfered edge 59 of the segmental element 54, forces the leaves of the element to open into the intervertebral space. The insertion of the segmental element can be achieved using a tool which is screwed onto the thread at the proximal end of the screw 53, or by means of a tool for applying linear pressure, such as by pushing manually. Once the leaves of the element have deployed, additional elements can be inserted until the intervertebral space has been filled to provide the correct level of support, which can help also in decompressing stenosis. Once this is achieved, a nut 60, threaded on both its inner core and its outer surface, may be screwed onto the proximal threaded end 61 of the screw 53, the outer thread thereby firmly locking the screw to the cortical bone of the pedicle of the inferior vertebra, and completing the procedure for one side of the vertebrae. This may then be repeated on the other side of the vertebra.

In an alternative exemplary implementation, the screw may be left without a locking nut so that the compression between the vertebrae is supported only by the segmented support insert. This arrangement may be advantageous when some degree of motion is desired between the vertebrae, such as when dynamic stabilization is desired rather than fusion. Dynamic stabilization requires the maintenance of angular rotation of one vertebra relative to its neighbor, and also motion along the screw axis to enable the vertebrae to move mutually linearly as the spine bends. In order to achieve this, the screw should not be fixed rigidly at both ends, but rather only at one end, either in the superior body, or at the inferior vertebra's pedicle, and it should be provided with some freedom within the bore. The screw, or more accurately the rod, may even be constrained in its bore by means of a screwed cap at the pedicle end, which allows it free motion, but does not allow it to come out of its bore. In this case, it merely acts as a central guide to hold the segmental elements in place, which can move up and down the rod with bending of the spine. In this case, in order to maintain intersegmental flexibility, the leaves of the segmental elements need not be fully flat, but can be shaped, for instance, like spring or dished washers, as will be illustrated in FIGS. 8A and 8B hereinbelow. Furthermore, for dynamic stabilization use, instead of the screw, a rod unfixed into the superior vertebral body may be used, though it may then be advisable that the locking nut at the pedicular end be used to provide some positive attachment of the rod. As yet another alternative, this locking nut could be used as a cap, in that it be threaded only externally for screwing into the pedicle's cortical bone but not onto the rod.

The arrangement shown in FIG. 5 is meant to show only example of implementing the intervertebral support system described in the present disclosure, and it is to be understood that variations of the screw design, and of the segmental elements and their method of deployment can be equally well used without limiting the scope of the protection sought.

Figure 6A:
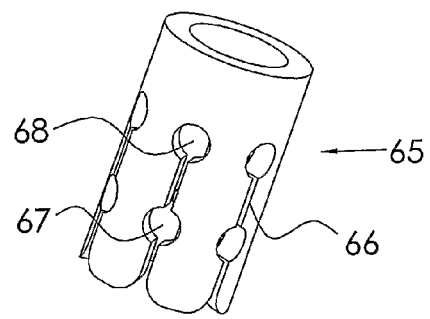
FIGS. 6A to 6D illustrate various stages of the insertion and expansion of an exemplary segmental element of cylindrical shape.
Figure 6B:
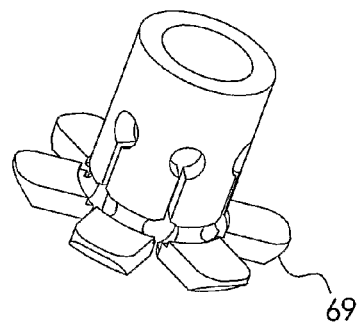
Figure 6C:
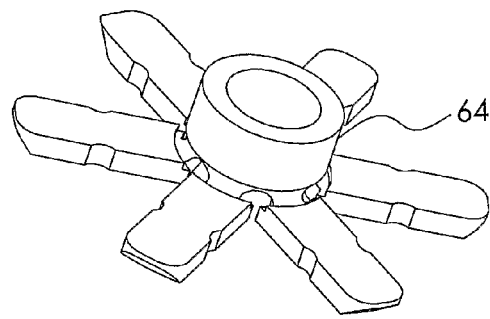
Figure 6D:
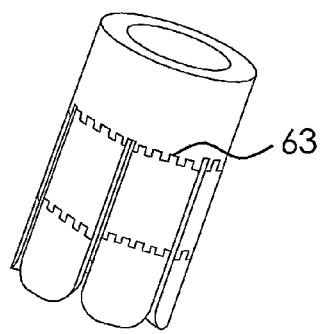

Reference is now made to FIGS. 6A to 6C, which illustrate various stages of the insertion and expansion of another exemplary segmental element 65 used for generating the complete segmented support insert. The example element of FIG. 6A is of cylindrical shape and has a number of longitudinal slits from what is defined as the distal end, along a major part of its length, the slits being positioned at spaced angular locations around its circumference. The slits may have a number of holes drilled along their length to weaken the walls of the cylinder at the positions of these holes. These holes should optimally be drilled in the same place longitudinally for all of the slits so that the walls of the cylinder are weaker at the longitudinal position of these holes, and the walls can thus bend more readily between these holes. In the example shown in FIGS. 6A-C two holes 67, 68 are shown on each of six slits. The element is inserted over the screw and is pushed from its proximal end down towards the intervertebral space. The distal end of the cylindrical element may have a chamfered edge 69, sloped towards the inner bore, so that when the distal end meets the shoulder 58 of the screw, the individual slotted sections of the wall of the cylindrical element bend outwards as shown in FIG. 6B, to form the "leaves" of the segmental element. As the cylindrical element is pushed even further down the screw, the upper slotted section of the wall of the element also bends radially outwards, and the lower part is then bent backward to be aligned with the upper section, until both slotted sections form a flat washer-like segmental element. The slotted walls of the cylindrical element shown in FIGS. 6A-C bend under pressure by virtue of the holes drilled in the cylindrical walls which weaken the walls at those points. It is to be understood that this is only one method by which the split walls are induced to bend at the desired point, and that other alternative methods may equally well be used. For instance, a groove can be cut circumferentially in the wall of the cylinder at a point at which the walls are intended to bend or even a mechanical joint used 63, as shown in FIG. 6D.

Figure 7A:
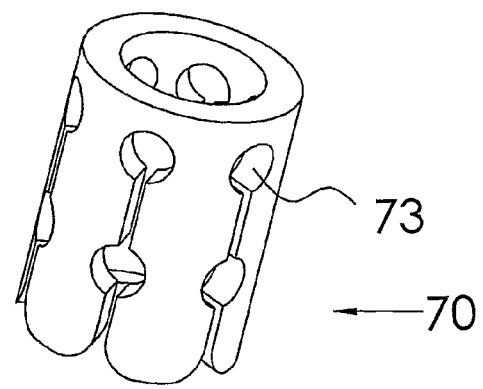
FIGS. 7A to 7C illustrate schematically an alternative cylindrical element to that of FIGS. 6A-D, and which opens completely flat when deployed
Figure 7B:
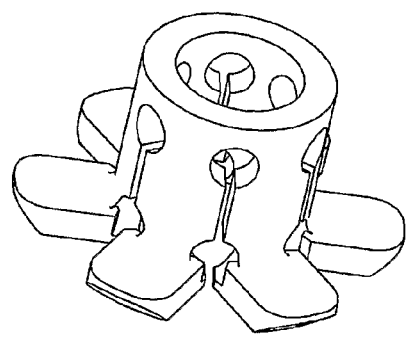
Figure 7C:
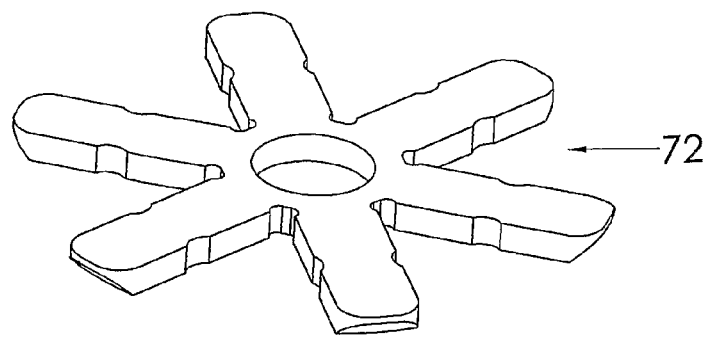

The final washer-like element shown in FIG. 6C has a remnant 64 of the cylinder at its central bore position, and this may not adapted so readily for efficient stacking. Reference is therefore now made to FIGS. 7A-C, which illustrate schematically an alternative cylindrical element 70, which opens flat when deployed 72. In this element the proximal holes 73 are drilled very close to the proximal end such that when the element is deployed and pressure applied thereto, it acquires a virtually flat configuration as shown in FIG. 7C.

Figure 8A:
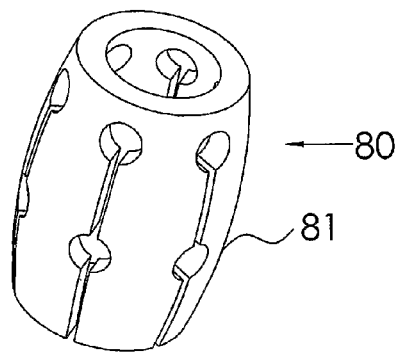
FIGS. 8A and 8B illustrate schematically an alternative cylindrical element to that of FIGS. 7A-C, which opens to a slightly curved form when deployed.
Figure 8B:
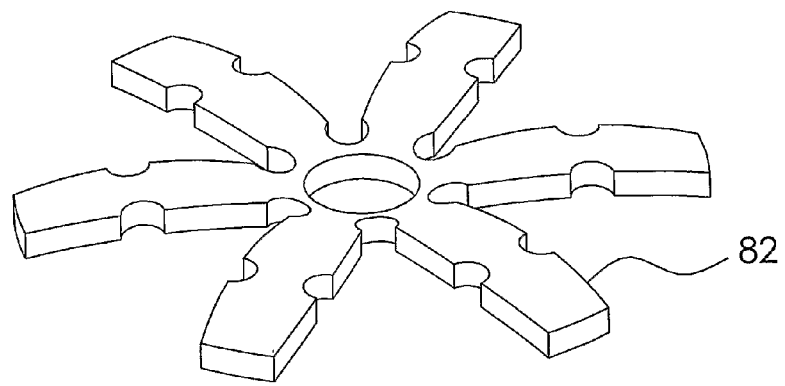

Reference is now made to FIGS. 8A and 8B which illustrate schematically an exemplary cylindrical element 80, similar to that shown in FIGS. 7A to 7C, but which is constructed having a slight barrel shape 81, so that when it opens in the intervertebral space, the leaves 82 of the segmental element have a slightly dished form so that they can be more advantageously used in dynamic stabilization applications requiring mutual vertebral displacement which flat, washer-like elements may impede, and for providing some level of springiness, which flat, washer-like elements do not generally provide.

In conclusion, one advantage on this support system is that it is possible to insert the segmental elements for generating the segmented insert through the same hole as that made for the GOLIF screw, resulting in only two holes for each level of stabilization, in contrast to the four holes for the screws used in the pedicle screw approach. Additionally there is no need for the additional incisions needed in the prior art methods using connecting rods or in the transverse approach of cage insertion. Furthermore, the combination of the screw and the segmental support insert provides support for both flexion and extension loads. Moreover, this procedure can be completed in a minimally invasive manner—an approach not entirely possible with current spine stabilization technology.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. An intervertebral support system comprising:
   a rod having a first end section adapted for post-operative affixing in the body of a first vertebra of a subject, the rod being dimensioned to be inserted through a bore in a pedicle of a second vertebra of said subject, adjacent to said first vertebra;
   a plurality of separate solid elements having lateral dimensions substantially larger than that of said bore disposed on said rod in a stack directed between the end faces of said first and second vertebrae of said subject, in the intervertebral region, when said rod is fixed in the body of said first vertebra; and at least one additional element strung onto said rod, which is dimensioned to pass through said bore and which is irreversibly expandable to a lateral diameter substantially larger than that of said bore, such that said stack can provide intervertebral support between said two adjacent vertebrae of said subject.

2. A system according to claim 1, wherein said at least one additional element comprises a cylinder whose wall includes slotted sections formed by a number of longitudinal slots along a part of its length, said longitudinal slots being positioned at angular locations spaced around the circumference of said cylinder.

3. A system according to claim 2, wherein said slotted sections of said wall of said cylinder are such that when they are bent radially outwards within said intervertabral region, said at least one additional element forms one of said plurality of separate solid elements having lateral dimensions substantially larger than that of said bore.

4. A system according to claim 2, said at least one additional element further comprising at least one mechanical joint formed in said cylinder wall, such that a slotted section of said wall bends preferentially at said at least one mechanical joint.

5. A system according to claim 2, wherein an end of said cylinder from which said longitudinal slots commence, is chamfered in a direction which assists in said radially outward bending of said slotted sections of said wall.

6. A system according to claim 3, said at least one additional element further comprising regions of said slots having widened dimensions, such that said slotted sections of said wall bend preferentially at said regions.

7. A system according to claim 3, said at least one additional element further comprising at least one circumferential groove formed on said cylinder wall, such that said slotted sections of said wall bend preferentially at said at least one circumferential groove.

8. A system according to claim 3, wherein said rod has a sloped shoulder to contact an end of said cylinder, to assist in said radially outward bending of said slotted sections of said wall.

9. A system according to claim 1, wherein when said at least one additional element is passed through said bore and is expanded to said lateral dimension substantially larger than that of said bore, and is added to said stack, said stack substantially fills the height of said intervertebral region.

10. A system according to claim 9, wherein said stack of elements and said rod provide support between said adjacent vertebrae.

11. A system according to claim 1 wherein said rod has a second end section having a threaded portion adapted to be affixed into said pedicle of said second vertebra.

12. A system according to claim 11, further comprising a cap adapted to be fixed to said pedicle to prevent said rod from retracting from said vertebrae.

13. A system according to claim 1, and wherein each element of said plurality of separate solid elements has either a flattened form or a dished form.

14. A system according to claim 1, wherein said first end section adapted for affixing in the body of a first vertebra rod (a) is a threaded section adapted to be screwed into said body of said first vertebra,
(b) has at least one opening arranged to receive bone cement or bone growth material so as to create a bond to said body of said first vertebra, or
(c) is adapted to be inserted as a forced fit into a hole formed in said body of said first vertebra.

15. A system according to claim 1 and wherein at least one of said elements comprises a shape memory alloy.

16. An intervertebral support system comprising:
a rod having a first end section adapted for affixing in the body of a first vertebra of a subject, the rod being dimensioned to be inserted through a bore in a pedicle of a second vertebra of said subject, adjacent to said first vertebra;
a plurality of separate solid elements having lateral dimensions substantially larger than that of said bore, disposed on said rod in a stack directed between the end faces of said first and second vertebrae of said subject in the intervertebral region when said rod is fixed in the body of said first vertebra, such that said stack provides intervertebral support between said two adjacent vertebrae of a subject,
wherein at least one of said separate solid elements has an undeployed configuration dimensioned to pass through said bore, and a deployed configuration having lateral dimensions substantially larger than that of said bore.

17. A system according to claim 16, wherein said undeployed configuration of at least one of said separate solid elements comprises a cylinder whose wall include slotted sections formed by a number of longitudinal slots along a part of its length, said longitudinal slots being positioned at angular locations spaced around the circumference of said cylinder.

18. A system according to claim 17, wherein said slotted sections of said wall of said cylinder are such that when they are bent radially outwards, said undeployed-configuration of said at least one separate solid element converts to said deployed configuration.

19. A it for providing intervertebral support, comprising:
a rod having a first end section adapted for affixing in the body of a first vertebra of a subject, the rod being dimensioned to be inserted through a bore in a pedicle of a second vertebra of said subject, adjacent to said first vertebra;
a plurality of separate solid elements having central openings for stringing on said rod, said elements having two states, a deployed state having lateral dimensions substantially larger than that of said bore; and a non-deployed state having lateral dimensions smaller than said bore, such that said elements can be threaded onto said rod in said undeployed state; and
a deploying mechanism to switch said elements from their undeployed state to their deployed state.

20. A kit according to claim 19, wherein said deploying mechanism comprises a sloped shoulder formed on said rod and a pushing device configured to force said elements over said shoulder to deploy said elements.

* * * * *